United States Patent [19]

Wallace

[11] Patent Number: 5,112,324
[45] Date of Patent: May 12, 1992

[54] URINAL AND INCONTINENCE APPARATUS

[76] Inventor: Rodney Wallace, 1113 Funston Ave., Pacific Grove, Calif. 93950

[21] Appl. No.: 759,897

[22] Filed: Sep. 13, 1991

[51] Int. Cl.$^5$ ............................................. A61F 5/44
[52] U.S. Cl. ..................................................... 604/349
[58] Field of Search ............... 604/350, 346, 347, 349; 623/12, 14; 251/4, 212

[56] References Cited

U.S. PATENT DOCUMENTS

| | | | |
|---|---|---|---|
| 2,663,467 | 12/1953 | Douglass et al. | 222/507 |
| 3,188,070 | 6/1965 | Lee | 266/41 |
| 3,366,363 | 1/1968 | Hogan et al. | 251/4 |
| 3,371,906 | 3/1968 | Lubold | 251/4 |
| 3,383,131 | 5/1968 | Rosfelder | 294/69 |
| 4,030,629 | 6/1977 | Melnikov | 220/211 |
| 4,092,010 | 5/1978 | Carlson, Jr. | 251/4 |
| 4,412,669 | 11/1983 | Hanyu et al. | 251/4 |
| 4,523,737 | 6/1985 | Wentworth | 251/4 |
| 4,705,518 | 11/1987 | Baker et al. | 623/14 |

Primary Examiner—Randy C. Shay
Assistant Examiner—Gina M. Gualtieri
Attorney, Agent, or Firm—Flehr, Hohbach, Test, Albritton & Herbert

[57] ABSTRACT

A urinal or incontinence apparatus is disclosed which employs elastic tubular membranes that are opened and closed by collars mounted for coaxial relative rotation. In one embodiment a pair of the membranes are mounted so that when the collars are turned in one rotational sense, one of the membranes is twisted to constrict towards a closed position forming a seal about the penis while the other membrane is twisted so as to expand toward an open position. At the neutral position, elastic counterforces created in the membranes are in balance so that the membranes are held in their partially open positions for insertion or removal. When the collar is moved beyond the neutral position the elastic force in one membrane overbalances that of the other membrane, which is thereby maintained in its sealed position. When removed, the membranes operate by snap action so that one is maintained in its fully closed position preventing leakage from a urine collection bag. In another embodiment a single flexible membrane is attached at its ends to a pair of collars which are threadably mounted together. As the collars are screwed together, the membrane constricts until it reaches its closed position when rotation of the collars is stopped by the threads.

15 Claims, 3 Drawing Sheets

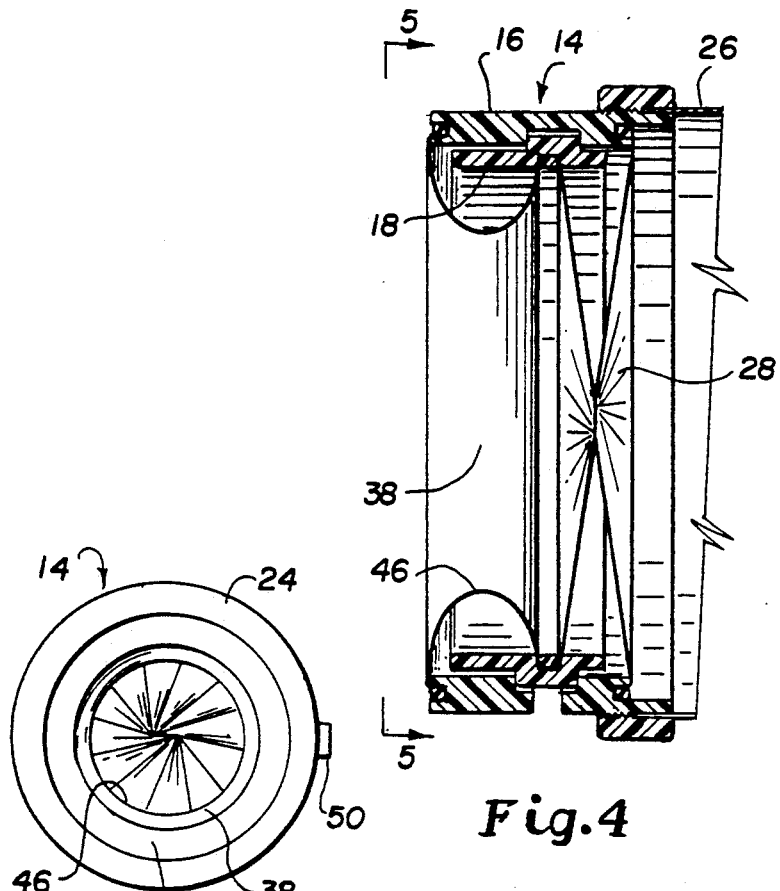

URINAL AND INCONTINENCE APPARATUS

BACKGROUND OF THE INVENTION

1. Field of the Invention

This invention relates in general to urinal and incontinence control for the human male. More specifically, the invention relates to urinals for use with bed-ridden male patients and for control of incontinence.

2. Description of the Prior Art

Heretofore hospitals and medical clinics have employed various types of urinal devices for bed-ridden male patients. Among these prior devices is the external catheter comprised of a condom with a hole for directing urine to a collection bag and adhesive gum for adhering the catheter to the patient's skin. Conventional external catheters of this type are not completely satisfactory in that they tend to come off the patient, and the adhesive seal can be easily broken resulting in leakage. The condoms are also relatively difficult to be placed on and removed from the patient. The need has been recognized for an improved urinal which is easier to use, is more secure against dislodgment and provides an effective seal over a longer period of time.

Various types of urine collection bags have been also provided in the prior art for control of male incontinence. Incontinence devices find use with paraplegics and other disabled persons who desire mobility. The prior art incontinence devices have a number of limitations and drawbacks. These include difficulties in maintaining the devices on the user over a period of time, and the tendency of the devices to leak.

OBJECTS AND SUMMARY OF THE INVENTION

It is a general object of the invention to provide new and improved apparatus for use as a urinal and for incontinence control which obviates the disadvantages and limitations of the prior art devices in this field.

Another object is to provide apparatus for use as a urinal or incontinence device which can be easily secured to the human penis and can be worn without discomfort.

Another object is to provide apparatus of the type described which maintains a secure seal about the penis for collecting urine without unintended leakage.

The invention in summary provides a urinal and incontinence device comprised of first and second annular collars which define a passageway that fits about the human penis. In one embodiment an elastic tubular membrane is attached at one end around a circumference of a first collar and at its opposite end around a circumference of the second collar. Operating means causes the collars to undergo relative rotation. When the collars are rotated in one sense the membrane is twisted toward a constricted opening at a closed position forming a fluid-tight seal about the penis. When the collars are rotated in the opposite sense the membrane twists toward an expanded opening at an open position. Collecting means is provided for collecting urine when the membrane is in its closed position. In another embodiment an additional membrane is mounted between the collars. Operating means causes the collars to rotate in one sense where the first membrane is twisted toward its constricted opening while the additional membrane is twisted toward its expanded opening, and when rotated in the opposite sense the first membrane is twisted toward its expanded opening while the additional membrane is twisted toward its constricted opening.

The foregoing and additional objects and features of the invention will appear from the following specification in which the several embodiments have been set forth in detail in conjunction with the accompanying drawings.

BRIEF DESCRIPTION OF THE DRAWINGS

FIG. 4 is an axial section view similar to FIG. 2 showing the elements in a further operating position;

FIG. 5 is an end elevation view to a reduced scale of the apparatus taken along the line 5—5 of FIG. 4;

FIG. 6 is an end elevation view to a reduced scale of the apparatus taken along the line 6—6 of FIG. 2;

FIG. 7 is an end elevation view to a reduced scale of the apparatus taken along the line 7—7 of FIG. 3;

DESCRIPTION OF THE PREFERRED EMBODIMENTS

Figure 1:
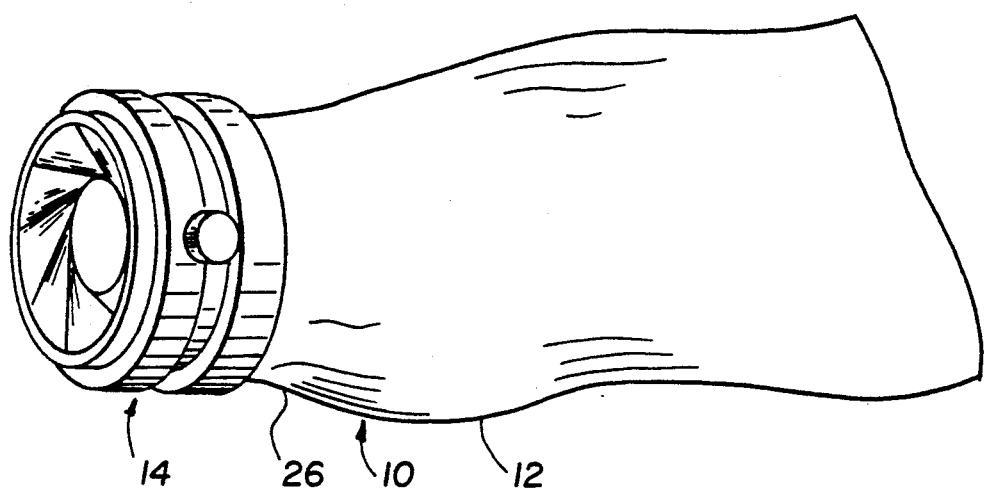
FIG. 1 is a perspective view of apparatus according to one embodiment of the invention.

In the drawings FIG. 1 illustrates generally at 10 apparatus according to one embodiment of the invention for use as a urinal or incontinence device to collect urine from the human penis. Apparatus 10 includes a flexible urine collection bag 12 attached at its open end to a valve assembly 14 which releasably mounts about the penis.

Valve assembly 14 is shown in detail in FIGS. 2-7 and comprises a first annular collar 16 together with a smaller diameter second annular collar 18 which is mounted for coaxial rotation within the first collar. A ring 20 on the outer surface of the second collar rotatably fits within a groove 22 formed within the first collar. A retaining bushing 24 is threadably mounted on the proximal end of the first collar for releasably capturing the open end 26 of collection bag 12.

Figure 3:
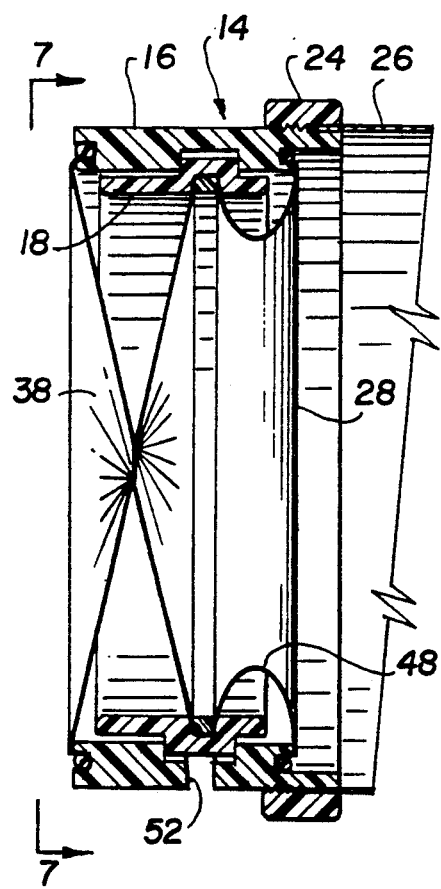
FIG. 3 is an axial section view similar to FIG. 2 showing the elements in another operating position.

A first elastic tubular membrane 28 is provided, and one of its ends 30 is attached around a circumference of the first collar near the latter's proximal end. This end of the membrane is captured within a circular groove formed in the first collar by suitable means, such as the O-ring seal 32. Opposite end 34 of the first membrane is attached around an inner circumference of the second collar at a position axially spaced from the circumference on the first collar at which the other end of the membrane is attached. The opposite end of the membrane is captured by a lock ring 36 which seats within a groove formed at the mid-span of second collar 18. An additional elastic tubular membrane 38 is provided, and its outer end 40 is attached around a circumference of the distal end of the first collar. This end of the membrane is secured within an annular groove by suitable means such as O-ring 42. The additional membrane's inner end 44 is secured around a circumference of the second collar by being captured by the lock ring 36. The membranes have respective mid-portions 46, 48 with radial lengths longer than the distances between their points of attachment to the collars so that when the membranes are under minimal tension they curve toward the center axis, as illustrated in FIG. 3. Preferably the membranes are comprised of a tough and flexible elastic material such as latex rubber, a suitable synthetic polymer or a composition rubber.

Operating means is provided for selectively causing relative rotation between the collars and comprises an operating arm 50 secured to and extending radially outwardly from second collar 18. The shank of the operating arm projects through a slot 52 formed in the first collar through 185° of arc about the collar's circumference.

Each membrane in association with the rotating collars provides a flexible valve similar to an iris valve. In this type of valve, relative rotation of the collars, while the axial distance between the points of attachment to the membrane remain constant, causes the mid-portions of the membranes to twist toward and away from constricted circular openings.

Figure 2:
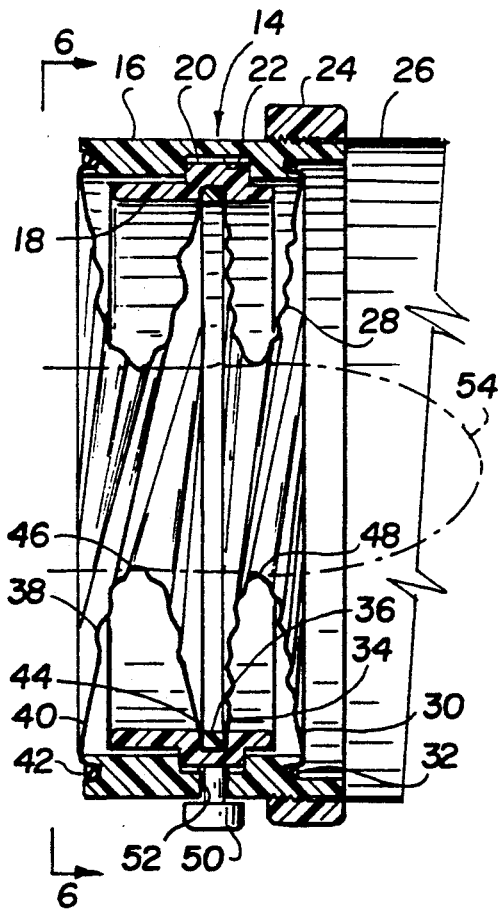
FIG. 2 is an axially section view to an enlarged scale of components of the apparatus of FIG. 1 showing the elements in one operating position.

FIGS. 5, 6 and 7 illustrate the sequence of operation for the additional membrane. At the initial position with operating arm at the 0° position, additional membrane 38 is under minimum tension so that its mid-portion 46 is expanded to the fully open position, as also shown in FIG. 4. Operating arm 50 is then manually turned so that second collar is rotated 90° relative to the first collar to the ready position shown in FIGS. 6 and 2. During this rotation the elastic counterforces in the membrane gradually increase. At the 90° position the additional membrane is partially open to a sufficient diameter which permits the device to be inserted about or removed from penis 54, as illustrated in FIG. 2. Further movement of the operating arm beyond the 90° position causes the membrane to snap toward a further constricted opening so as to close about the penis and form a fluid-tight seal which is sufficient to prevent leakage of urine. The apparatus is removed by manually moving the arm back to a position at 90° or less arc, which opens the additional membrane sufficient to release it from the penis.

With the apparatus removed from the penis, the operating arm is moved up to the 180° point of travel, which twists and constricts the additional membrane to the fully closed position. This action further increases the elastic counterforce in the membrane, which substantially reaches a maximum at the 180° position. Overtravel movement of the operating arm to the 185° position shown in FIG. 7 creates an elastic locking force which tends to hold the membrane in its fully closed position. That is, the resultant elastic forces in the membrane at the 185° position create a torque urging the second collar in the clockwise direction, as viewed in FIG. 7. This locking force can be released by manually turning the operating arm back through the 180° position.

First membrane 28 is sized and positioned so that, when the collars are turned in either rotational sense, opening and closing of the first membrane is out of phase with that of the additional membrane. This provides a bistable valve arrangement which facilitates easy insertion and removal on the patient while ensuring automatic full closure of the urinal bag opening when the apparatus is removed. The mode of operation of apparatus 10 which achieves these results is as follows:

Apparatus 10 is prepared for insertion by turning operating arm to substantially the 90° position illustrated in FIG. 6. At this point first membrane 28 and additional membrane 38 are in their partially open positions of substantially equal inner diameters. The elastic counterforces in the two membranes are substantially equal and in balance, that is the elastic force in one membrane acts in a direction which substantially balances the elastic force in the other membrane. The apparatus with its bag attached is then slipped over the penis. The operating arm is then moved beyond the 90° position, i.e. clockwise as viewed in FIG. 6, for a further arc of travel, which can be from 5° to 20° or more beyond the 90° position, depending upon the size of the penis. As the operating arm moves beyond the 90° position, additional membrane 38 twists further toward its constricted opening where it closes about the penis in a fluid-tight seal. This is a snap action closure in that as operating arm 50 moves beyond the 90° position the elastic forces within the additional membrane as the latter constricts become greater than the elastic forces within the first membrane as it expands. The resultant of these two forces acts in a direction to urge the additional membrane toward its closed position, thereby maintaining a light pressure on the penis for sealing against fluid leakage, but not so tight as to create an undesirable tourniquet effect. Urine can then be collected in bag 12. As desired, a suitable draining tube, not shown, can be connected with the bag for directing urine away for disposal.

For removal of the collection bag, operating arm is moved back to or beyond the 90° position of FIG. 6. This counter-rotates the collars so that additional membrane 38 is expanded while first membrane 28 is partially constricted to the neutral position. After the collars are removed from the penis, the operating arm can be moved through a short arc of travel on either side of the 90° position, for example to the 85° position. The overbalance of elastic forces in the two membranes causes further expansion of the additional membrane until it reaches its fully open position at the 0° point. At the same time, first membrane 28 is twisted to its constricted, fully closed position. The elastic forces in the first membrane at this position are sufficiently strong to keep the restriction fully closed. The first membrane in this position thereby forms a fluid-tight seal which prevents egress of urine from the bag. It is a characteristic of the elastic closing force that the first membrane is firmly held in its closed position even where undergoing shock, such as when the valve assembly and bag may be accidentally dropped on the floor. It is also a characteristic of the invention that when in the closed position about the penis the elastic holding force is automatically maintained even when the patient moves, and without injury to the patient.

Figure 8:
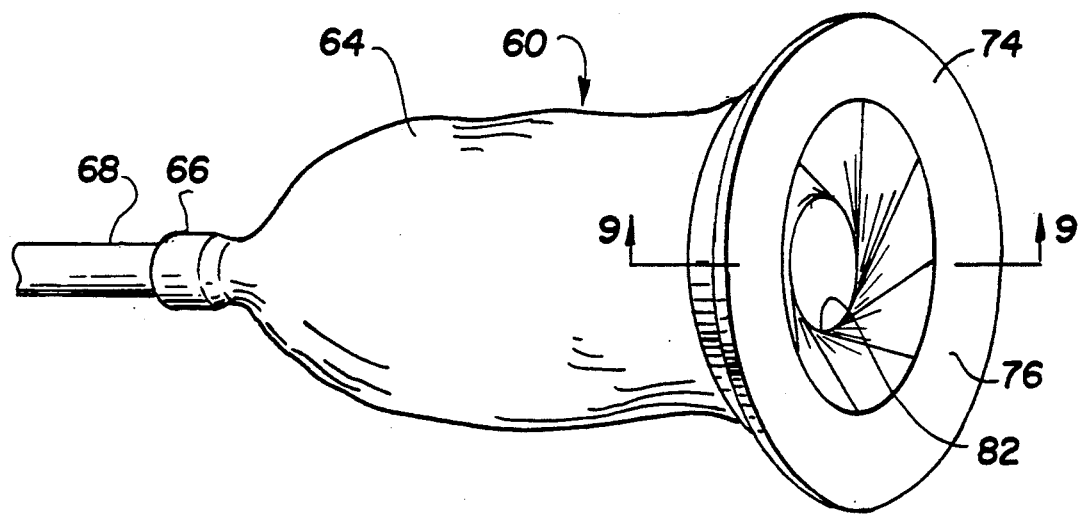
FIG. 8 is a perspective view of apparatus according to another embodiment of the invention for use as an incontinence device.
Figure 9:
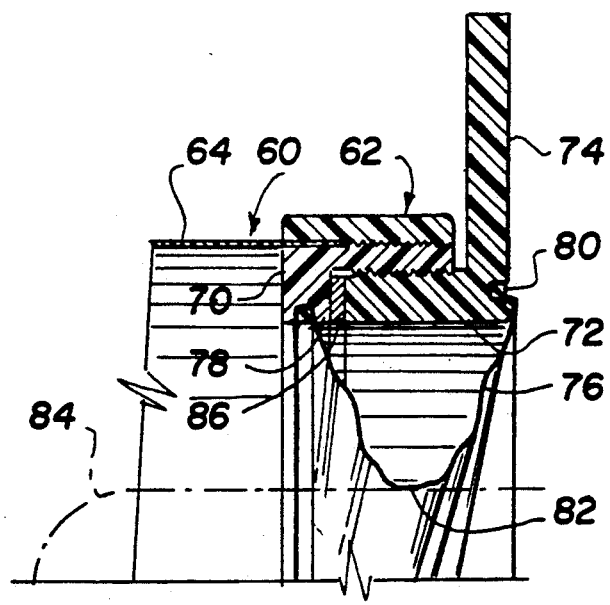
FIG. 9 is a fragmentary axial section view taken along the line 9—9 of FIG. 8.

FIGS. 8 and 9 illustrate another embodiment providing apparatus 60 which is specially adapted as an incontinence device, for example for use with paraplegics and disabled people who need mobility. Apparatus 60 is comprised of a valve assembly 62 attached to one end of a urine collection sheath 64, which can be of a suitable rubber or plastic material. One end of the sheath is formed with a neck 66 having an opening which fits about the end of a urine collection bag or drain tube 68.

Valve assembly 62 is comprised of a first or outer collar 70 formed with internal threads and a second or inner collar 72 formed with external threads which screw into the threads of the outer collar. A flat annular rim 74 is attached to the distal end of the outer collar for use with a suitable belt, not shown, which can be used for attaching the apparatus to the patient.

An elastic tubular membrane 76 is provided and is formed of a suitable tough and flexible latex rubber or synthetic polymer material. One end 78 of the membrane is attached around the circumference of the outer collar at its proximal end, and the other end 80 is attached around the circumference of the inner collar at a position which is axially spaced from the point of attachment to the first collar. The membrane is sized and positioned so that its mid-portion 82 twists toward a constricted opening to close about the penis 84 when the collars undergo relative rotation as they are manually turned on their threads.

Right-hand threads can advantageously be formed in the two collars. Apparatus 10 is prepared in its ready position for insertion by partially unscrewing in a left-hand sense outer collar 70. The resulting relative rotation of the collars causes membrane 76 to twist to its partially open position with an inner diameter sufficient to insert over the penis. After insertion, the outer collar is screwed back in a right-hand sense until its threads reach the end of the threads of the inner collar. The thread length thereby creates a stop limiting the degree of collar rotation. As the outer collar is screwed to its stop, the membrane is twisted to the constricted opening at its closed position about the penis. The stop prevents the membrane from over tightening about the penis, which could cause injury. Friction in the threads of the collars prevents unintended counter-rotation so that the membrane is maintained in its closed position until the collars are manually unscrewed, such as when it is desired to remove the urine collection bag. The minimum diameter of the membrane's opening at its closed position can be selectively adjusted by inserting or removing one or more shims or washers 86 which are mounted in the annular space at the base of the threads between the inner and outer collars. This permits the apparatus to be adjusted for different size penises, for example for children as well as adults.

While the foregoing embodiments are at present considered to be preferred it is understood that numerous variations and modifications may be made therein by those skilled in the art and it is intended to cover in the appended claims all such variations and modifications as fall within the true spirit and scope of the invention.

What is claimed is:

1. Apparatus for use as a urinal or incontinence device to collect urine from a human penis, comprising the combination of first and second annular collars defining a passageway sized to fit about the penis, means for mounting the collars for coaxial relative rotation, an elastic tubular membrane having one end attached around a circumference of the first collar and having an opposite end attached around a circumference of the second collar at a position which is axially spaced from the circumference of the first collar, said tubular membrane having a mid-portion which extends between said ends, operating means for selectively causing relative rotation between the collars in one rotational sense for twisting the mid-portion of the membrane toward a constricted opening at a position about the penis to form a fluid-tight seal therewith, said operating means further causing relative rotation between the collars in a rotational sense which is opposite said one sense for twisting the mid-portion of the membrane toward an expanded opening at an open position radially spaced about the penis and collecting means attached to one of said collars for collecting urine from the penis when the membrane is in a closed position.

2. Apparatus as in claim 1 in which the first and second collars each have inner cylindrical walls and the mid-portion of said tubular membrane is positioned radially inwardly of the cylindrical walls.

3. Apparatus as in claim 1 in which said collecting means comprises a flexible bag.

4. Apparatus as in claims 1 or 3 in which said means for causing said relative rotation selectively turns the collars through an arc of at least 180° of relative rotation when the apparatus is dismounted from the penis for twisting and constricting the mid-portion of the membrane toward a fully closed position to occlude said passageway for preventing egress of urine therethrough.

5. Apparatus as in claim 1 in which said means for causing said relative rotation selectively turns the collars through an arc of greater than the 180° of relative rotation when the apparatus is dismounted from the penis for twisting the membranes to a fully closed position with elastic counterforces in the membrane acting to releasably hold the membrane in said fully closed position to prevent egress of urine through the passageway.

6. Apparatus as in claim 1 in which the operating means includes means for limiting the constricted opening to a predetermined size commensurate with the size of the penis.

7. Apparatus as in claim 6 in which the means for limiting the constricted opening includes means providing complementary male and female threads on the first and second collars for providing said relative rotation, said threads having a predetermined thread length which limits the degree of relative rotation between the collars in said one rotational sense and thereby limits the degree of twisting of the membrane for limiting the constricted opening to said predetermined size.

8. Apparatus as in claim 7 in which said operating means includes means for selectively varying said predetermined size of the constricted opening including shim means fitted with the thread means for selectively varying the degree of relative rotation between the collars.

9. Apparatus as in claim 6 in which said collecting means comprises a flexible sheath, and an opening in the sheath attachable to a tube or collection bag for directing urine thereto.

10. Apparatus as in claim 1 in which said second collar is mounted coaxially within the first collar, and including an additional elastic tubular membrane having one end attached around the circumference of the first collar at a position which is axially spaced from the circumference at which said first-mentioned membrane is attached, said additional membrane having an opposite end attached around a circumference of the second collar, said operating means causing the collars to rotate in said opposite sense so that the additional membrane is twisted toward a constricted opening at a sealed position when the first-mentioned membrane is twisted toward its open position and further so that the relative rotation of the collars in said one sense causes the additional membrane to twist toward an expanded opening at an open position when the first-mentioned membrane is twisted toward its closed position.

11. Apparatus as in claim 10 in which said first-mentioned membrane and said additional membrane are sized and positioned so that when the collars undergo relative rotation in said one sense the constriction of the first-mentioned membrane creates a first elastic counterforce therein which urges the collars to rotate in said opposite sense, and when said collars undergo relative rotation in said opposite sense the constriction of said additional membrane creates a second elastic counterforce therein which urges the collars to rotate in said one sense.

12. Apparatus in claim 11 in which when said first-mentioned membrane is adjacent or at its closed position said first elastic counterforce is greater than said second elastic counterforce for releasably maintaining said first-mentioned membrane in its closed position, and when said additional membrane is in its closed position said second counterforce is greater than said first counterforce for releasably maintaining the additional membrane in its closed position.

13. Apparatus as in claim 10 in which the operating means includes an arm carried on the second collar and projecting outwardly therefrom for manually turning the second collar relative to the first collar.

14. Apparatus as in claim 10 in which said collecting means comprising a flexible bag.

15. Apparatus as in claim 10 in which both the opposite end of the first-mentioned membrane and the opposite end of the additional membrane are attached to circumferences of the second collar at a mid-portion thereof which is located between the opposite ends of the first collar.

* * * * *